(12) United States Patent
Mislavskij et al.

(10) Patent No.: US 11,996,272 B2
(45) Date of Patent: May 28, 2024

(54) METHOD AND DEVICE FOR PLASMA-CHEMICAL GAS/GAS MIXTURE CONVERSION

(71) Applicant: Boris Vladlenovich Mislavskij, Moscow (RU)

(72) Inventors: Boris Vladlenovich Mislavskij, Moscow (RU); Roman Lazirovich Iliev, Moscow (RU); Mikhail Yuryevich Marin, Moscow (RU); Evgeny Pavlovich Gorelik, Himki (RU)

(73) Assignee: Boris Mislavskij, Moscow (RU)

( * ) Notice: Subject to any disclaimer, the term of this patent is extended or adjusted under 35 U.S.C. 154(b) by 328 days.

(21) Appl. No.: 17/284,153

(22) PCT Filed: Oct. 10, 2019

(86) PCT No.: PCT/RU2019/000696
§ 371 (c)(1),
(2) Date: Apr. 9, 2021

(87) PCT Pub. No.: WO2020/076186
PCT Pub. Date: Apr. 16, 2020

(65) Prior Publication Data
US 2021/0335580 A1    Oct. 28, 2021

(30) Foreign Application Priority Data
Oct. 12, 2018   (RU) ................................ 2018136120

(51) Int. Cl.
*H01J 37/32*  (2006.01)
*B01J 19/08*  (2006.01)
(Continued)

(52) U.S. Cl.
CPC ....... *H01J 37/32449* (2013.01); *B01J 19/088* (2013.01); *H01J 37/32541* (2013.01);
(Continued)

(58) Field of Classification Search
CPC .......... H01J 37/32449; H01J 37/32541; B01J 19/088; B01J 2219/0809; B01J 2219/083;
(Continued)

(56) References Cited

U.S. PATENT DOCUMENTS 5,866,081 A * 2/1999 Williamson ........... B01D 53/32
60/275
2003/0108460 A1* 6/2003 Andreev ................. A61L 2/202
422/186.07
(Continued)

FOREIGN PATENT DOCUMENTS

JP    2001190926 A    7/2001
JP    2005147125 A1   6/2005
(Continued)

*Primary Examiner* — Abdullah A Riyami
*Assistant Examiner* — Syed M Kaiser
(74) *Attorney, Agent, or Firm* — The Roy Gross Law Firm, LLC; Roy Gross

(57) ABSTRACT

A method and a device are proposed for plasma-chemical conversion of gas or gas mixture using a pulsed electrical discharge. They allow increasing efficiency of the process for converting gas/gas mixture into desired products by stimulating forward reactions and minimizing reverse reactions. This is achieved by converting the gas/gas mixture using a pulsed electrical discharge in the form of hot plasma channels formed between electrodes in the moving flow of gas/gas mixture, wherein the ratio of the flow velocity to the average discharge current falls within the following range: 250 J/(m³*A²)<ρ*V²/I²<4,000 J/(m³*A²), where ρ is the density of gas/gas mixture in a reaction chamber (kg/m3), V is the flow velocity of gas/gas mixture in the reaction
(Continued)

chamber (m/s), and I is the average current of the pulsed electrical discharge (A).

H05H 1/4697; C07C 2/80; C07C 11/24; C01B 3/342; C01B 3/00; Y02P 20/582
See application file for complete search history.

10 Claims, 2 Drawing Sheets

(56) References Cited

U.S. PATENT DOCUMENTS

| | | | |
|---|---|---|---|
| 2006/0071608 A1* | 4/2006 | Malik | H05H 1/24 |
| | | | 315/111.01 |
| 2010/0258429 A1 | 10/2010 | Ugolin | |
| 2016/0102025 A1* | 4/2016 | Nunnally | A01G 7/06 |
| | | | 422/162 |
| 2016/0290223 A1* | 10/2016 | Mills | F02B 65/00 |
| 2018/0221847 A1 | 8/2018 | Wong | |

(51) Int. Cl.
*H05H 1/24* (2006.01)
*H05H 1/48* (2006.01)

(52) U.S. Cl.
CPC ........ *H05H 1/48* (2013.01); *B01J 2219/0809* (2013.01); *B01J 2219/083* (2013.01); *B01J 2219/0871* (2013.01); *B01J 2219/0883* (2013.01); *H05H 1/4697* (2021.05)

(58) Field of Classification Search
CPC ........ B01J 2219/0871; B01J 2219/0883; B01J 19/2405; B01J 2219/0869; B01J 2219/0898; B01J 19/08; H05H 1/48;

FOREIGN PATENT DOCUMENTS

| | | | | |
|---|---|---|---|---|
| KR | 101160906 B1 | 6/2021 | | |
| WO | WO-2008011213 A2 * | 1/2008 | ............. | C03B 5/005 |
| WO | WO2009/057473 A1 | 5/2009 | | |
| WO | WO-2016044239 A1 * | 3/2016 | ................ | C02F 1/30 |

* cited by examiner

METHOD AND DEVICE FOR PLASMA-CHEMICAL GAS/GAS MIXTURE CONVERSION

CROSS-REFERENCE TO RELATED APPLICATIONS

This application is a U.S. national stage application of an international application PCT/RU2019/000696 filed on 10 Oct. 2019, whose disclosure is incorporated herein in its entirety by reference, which international application claims priority of a Russian Federation patent application RU2018136120 filed on 12 Oct. 2018.

FIELD OF THE INVENTION

The present disclosure is related to the field of chemistry, specifically it proposes a method for plasma-chemical conversion of gas or gas mixture using a pulsed electrical discharge. It can be used to process natural gas or associated petroleum gas in the petrochemical industry, or in environmentally friendly technologies for binding and processing carbon dioxide and in other types of petrochemical processes.

BACKGROUND OF THE INVENTION

Plasma can be regarded as a very powerful tool for facilitating chemical reactions with a high activation energy, for example, in the production of syngas, conversion of $CO_2$ and $H_2S$, etc. There are well known plasma-based technologies that utilize DBD and pulsed corona discharges, electric arc, or a microwave discharge to produce plasma-chemical reactions stimulated by hot or nonequilibrium plasma. Non-equilibrium plasma owes its name to the fact that the gas molecules remain relatively cold (their temperature does not increase), while the electrons have very high energy that is more than enough to disassociate and ionize molecules.

Optimization of the plasma parameters to produce a plasma-chemical reaction is to minimize energy cost while to maximize the yield of desired products. To stimulate forward chemical reactions, the plasma disassociates or excites the molecules of the reagents, producing radicals or other active particles, which can react with each other to achieve the desired products.

There are two ways to produce such reactions.

One of the ways is by disassociating the source molecules by means of colliding them directly with electrons that have sufficient energy. In this case, the key characteristic of the plasma is the voltage of the electric field, or rather the ratio of the electric field voltage to the concentration of the gas that determines whether the energy acquired by the electron in the electric field between two collisions with gas molecules is enough for the desired process of forming radicals or active particles.

This method is typical of all types of nonequilibrium plasma such as dielectric barrier discharge (DBD), including intermittent barrier discharge described in the article DBD in burst mode: solution for more efficient CO2 conversion? A. Oskan et al (see Plasma Sources Science and Technology, IOP Publishing, 2016, 25 (5), p. 055005), published at <<https://hal.sorbonne-universite.fr/hal-01367345>>.

The same applies to the nanosecond pulsed discharge as described, for example, in the article Nanosecond-Pulsed Discharge Plasma Splitting of Carbon Dioxide, Moon Soo Bak et al, (see IEEE TRANSACTIONS ON PLASMA SCIENCE, VOL. 43, NO. 4, April 2015, pp. 1002-1007).

Both works can be regarded as prior art to the present disclosure and have one major drawback—a very low conversion process efficiency.

One major problem of nonequilibrium plasma is that all types of energy losses of the electrons (including elastic collisions, vibrational excitation of molecules, etc.) that lead to heating up the gas are irreversible and, most importantly, useless in this case. Unfortunately, these types of losses are usually far greater than the molecule disassociation energy and heat (enthalpy) of the reaction. For this reason, the energy efficiency of nonequilibrium plasma (the rate of reaction enthalpy and energy cost) is usually very low—about 10%-20%.

The alternative is to heat the gas molecules in reaction chamber up to a temperature that is sufficient for them to break through the activation barrier of the reaction. In this case, the heating up is a useful process, and any processes resulting in more heat generation are not losses.

However, there is another problem when the reaction chamber is heated: all the molecules are heated, and the energy is spent not only on the heating and dissociation of the reagents that we need but also for heating and dissociating the final products of the reaction. In this case, the main problem is the reverse reactions that reduce the conversion rate and the energy efficiency of the process.

The solution is to remove the reaction products from the hot area as soon as possible. Due to this method of suppressing the reverse reactions, the yield of the desired products and the energy efficiency of the plasma-chemical processes can be substantially increased. This approach is sometimes called as quenching of the products of plasma-chemical reactions.

A technology for conducting plasma-chemical reactions is known, as described in patent U.S. Pat. No. 7,867,457 B2 published Jan. 11, 2011. It involves a special plasma-chemical reactor that uses a gliding arc that moves through a gas flow organized as a reverse vortex. This partially solves the problem of quenching of the products by having them move through the plasma channel, but this solution also has some major drawbacks stemming from the fact that the velocity of the plasma channel relative to the gas (the slippage velocity) is relatively low, at about 1 meter per second. Therefore, at least some of the reaction products manage to undergo secondary treatment, which leads to a significant contribution of reverse reactions and lowers the conversion rate and the energy efficiency of the process.

Ensuring optimal gas conversion conditions in the hot zone while ensuring effective quenching of the reaction products makes it possible to achieve maximum conversion as well as energy efficiency of the conversion process.

BRIEF SUMMARY OF THE INVENTION

The technical effect of the present disclosure is increased efficiency of the process of converting gas/gas mixture into the desired products by stimulating forward reactions and minimizing reverse reactions.

To achieve this effect, it is proposed to use a new method of plasma-chemical gas/gas mixture conversion process that involves creating a pulsed electrical discharge in the flow of the gas/gas mixture moving in the reaction chamber at a given velocity, which creates a short-lived plasma channels connecting the electrodes located inside the reaction chamber.

The proposed method solves the problem of quenching of the reaction products generated in the hot plasma channel. The gas/gas mixture flow moving at a given velocity in the reaction chamber is supplying new portions of reagents for the conversion while also helping quickly extinguish the plasma channel that has just formed, thereby limiting its duration. The optimal plasma-chemical conversion process is achieved when the ratio of the gas/gas mixture flow velocity in the reaction chamber to the average current in the electrical discharge is:

$$250\ J/(m^3*A^2)<\rho*V^2/I^2<4{,}000\ J/(m^3*A^2),$$

where $\rho$ is the density of the gas/gas mixture in the reaction chamber (kg/m$^3$), V is the flow velocity of the gas/gas mixture in the reaction chamber (m/s), and I is the average current of the discharge (A).

This method is implemented by building a special device for plasma-chemical conversion of gas/gas mixture comprising a reactor consisting of a reaction chamber and input/output modules, a high-voltage power supply unit connected to the electrodes inside the reaction chamber, and a gas flow rate regulator. The high-voltage power supply unit creates a pulsed electrical discharge between the electrodes in the form of a hot plasma channel lasting (10-500) ns and with a frequency of (20-300) kHz.

DETAILED DESCRIPTION OF THE INVENTION

Figure 1:
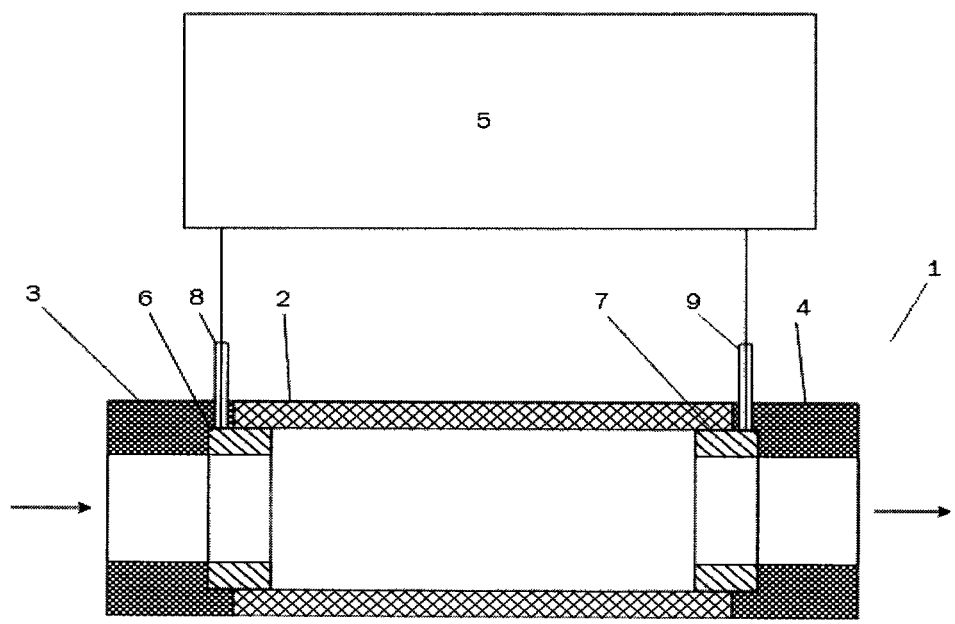
FIG. 1 depicts a diagram of the proposed gas/gas mixture plasma-chemical conversion device.

Plasma conversion of a gas or gas mixture into the desired product involves the dissociation or excitation of molecules of the initial reagents that do not enter into a chemical reaction without external action while preventing this effect on the reaction products formed to avoid reverse reactions. For example, when acetylene is produced from natural gas (methane), the methane molecules, but not the acetylene molecules, must be plasma treated, and when CO and hydrogen are produced from a mixture of CO2 and methane, the CO2 and CH4 initial reagents must be subject to treatment, and not the CO and H2 reaction products.

The idea behind the proposed gas conversion process is to create a gaseous area in the pulsed electrical discharge in the form of a hot plasma channel that connects the electrodes. The temperature inside the channel reaches several thousand degrees Celsius. The high temperature causes disassociation or excitation of the molecules in the gas inside the plasma channel. After the extinction of the plasma channel, the required chemical reaction takes place involving the radicals or excited gas particles, as a result of which the desired components are created, which then remain stable because now the temperature of the environment is no higher than (100-150)° C.

The efficiency of this gas conversion process assuming its continuous use depends directly on the form of the pulsed electrical discharges created. Maximum efficiency is achieved when the form of the pulsed electrical discharges are hot plasma channels that appear and reappear intermittently. An electric discharge in the form of an intermittent plasma channel is the optimal form of discharge for the process.

The parameters for generating the optimal discharge form in a gas flow moving at a given velocity are different from the parameters for creating the same type of discharge in stationary gas. In the course of conducting experiments, it was established that there is a correlation between the velocity of the gas flow and the average current of the pulsed electrical discharge needed to create the optimal discharge form in the given gas composition. The following range of values was determined for the ratio of the velocity of the gas flow to the average current of the discharge needed to maintain the optimal discharge form:

$$250\ J/(m^3*A^2)<\rho*V^2/I^2<4{,}000\ J/(m^3*A^2),$$

where $\rho$ is the density of the gas/gas mixture in the reaction chamber (kg/m$^3$), V is the flow velocity of the gas/gas mixture in the reaction chamber (m/s), and I is the average current of the discharge (A).

The velocity V of the gas/gas mixture flow used in the formula above is calculated as the ratio of the volume of the gas/gas mixture coming into the reaction chamber per unit of time to the cross-section area of the work zone of the reaction chamber. This velocity can be measured directly by means of the Doppler effect.

Using an intermittent pulsed electrical discharge in a moving gas flow makes it possible to solve several problems at the same time:

1) New portions of reagents needed for the conversion are constantly being supplied, making it possible to treat more reagents in less time.
2) The finished products of the reaction are quickly removed from the active zone of the reactor, thus minimizing the possibility of reverse reactions and boosting the efficiency of the conversion process.
3) The hot plasma channel gets blown over with the gas flow, thus helping better extinguish it and control its duration.

The duration of the plasma channel affects the efficiency of the gas conversion. If it is too short, not all the gas molecules in the channel get disassociated, and so the number of particles that can take part in the reaction is reduced, thereby the number of forward reactions that generate the desired products also decreases. If the plasma channel lasts too long, the hot temperature will impact not only the reagents but also the resultant molecules of the desired product causing them to disassociate and resulting in reverse reactions.

The optimal duration for the plasma channel to have a sufficiently high temperature and thus a sufficiently high degree of molecule ionization that ensures electrical resistance of the channel for less than 10,000 Ohm is (10-500) ns. If the duration of the plasma channel is less than 10 ns, the energy efficiency of the forward reaction decreases, and if it is longer than 500 ns, the impact of reverse reactions goes up, and the quenching effectiveness goes down.

Experiments also allowed determining the optimal frequency of the plasma channels for conducting plasma-chemical conversion, (20-300) kHz. At lower frequencies, the productivity of the reactor fell, and at higher frequencies, there were technical difficulties with regard to stabilizing the optimal form of the discharge.

The principle of conducting plasma-chemical gas/gas mixture conversion is described below using the diagram of the device given in FIG. 1.

The plasma-chemical gas/gas mixture conversion device comprises reactor 1, consisting of reaction chamber 2 and input 3 and output 4 modules, and high-voltage power supply unit 5 connected to electrodes 6 and 7 positioned inside reaction chamber 2.

Reaction chamber 2 is manufactured from a heat resistant dielectric material such as ceramic or quartz glass and will normally be shaped like a cylinder.

Electrodes 6 and 7 consist of an anode and cathode or several pairs of anodes and cathodes each with its own power supply, and they can take several shapes. For example, they can be shaped as a cylinder with a flat end, a cylinder that has one end with a sharp edge, a cylinder with rods or needles on one end, or a cone with a sharp end and radial holes. Any combination of design and shape is possible. The following materials can be used for the electrodes and their parts: steel, stainless steel, copper, brass, bronze, titanium, tungsten, molybdenum, hafnium, zirconium, or any combinations thereof.

Power supply unit 5 is connected to electrodes 6 and 7 via high-voltage terminals of anode 8 and cathode 9, respectively. The number of high voltage inputs 8, 9 for each electrode 6 and 7 may vary; their number is selected based on the required inductance of the discharge circuit to achieve the necessary plasma channel duration.

The initial gaseous reagent or several initial gaseous reagents whose flow rate is set by one or several gas flow regulators are fed into reactor 1 where they are directed to reaction chamber 2 through the holes of input module 3. Once in the reaction chamber, they start moving at a given velocity. High-voltage power supply unit 5 ensures that an intermittent hot plasma channel is created between electrodes 6 and 7 with optimal duration and frequency parameters to achieve plasma-chemical conversion. The sufficient flow velocity of reagents in reaction chamber 2 and the shape of electrodes 6 and 7 result in the plasma channel being quickly extinguished, which minimizes the possibility of reverse reactions. The components produced as a result of the conversion as well as the remaining reagents leave chamber 2 through the holes in output module 4 helping maintain the required gas velocity in the reaction chamber.

Figure 2:
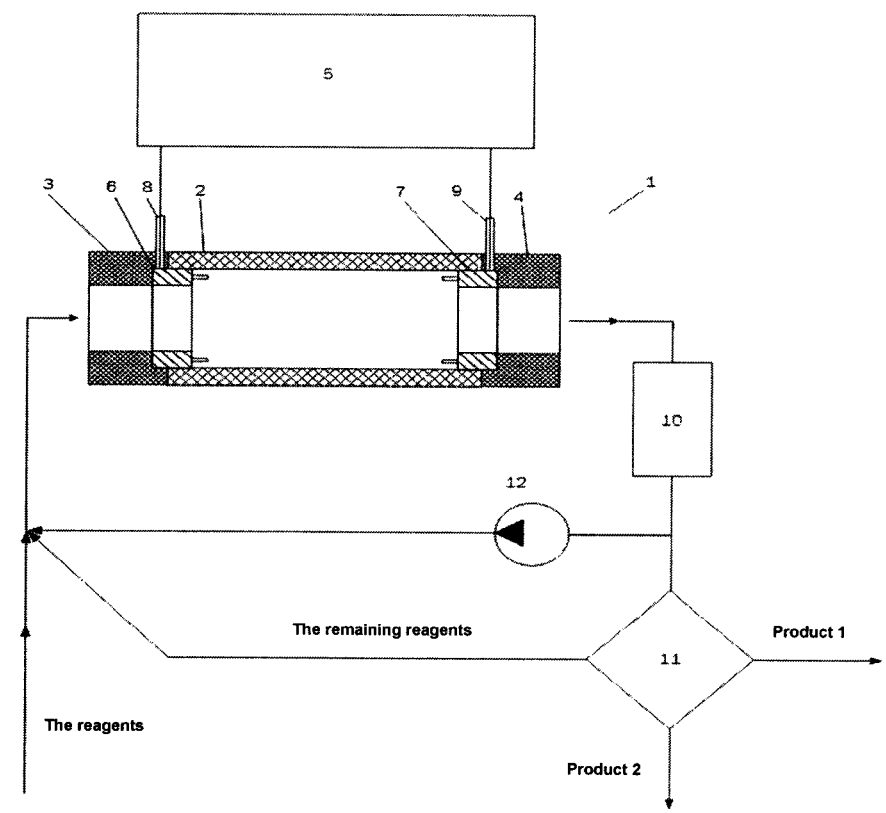
FIG. 2 depicts a gas/gas mixture plasma-chemical conversion device with repeat treatment of the gas/gas mixture.

FIG. 2 shows the version of the plasma-chemical conversion device in which the reagents that have not reacted can be once again directed into reaction chamber 2.

After the mix of reagents and conversion products leaves output module 4, it goes through recuperative heat exchanger 10 where it gets cooled down to a suitable temperature for the gas separation unit, and the mix is then fed into gas separation unit 11 where the products are separated from the reagents. The remaining reagents are then directed into the supply channel of the initial reagents and into reactor 1. The device can also be additionally equipped with recycling blower 12 to create the required gas flow rate in reaction chamber 2, if the velocity at which the initial reagents are fed from gas flow rate regulator 13 is insufficient.

Products 1 and 2 can be, for example, CO and oxygen, if $CO_2$ is the raw material used in the process. The system can also produce a single product, for example, acetylene from methane. Products do not have to be separate from each other, for example, if the goal is to produce syngas (a mixture of $H_2$ and CO) from a $CO_2$ and methane mixture.

One option for the design of gas separation module 11 could be a two-stage system similar to that used in the production of acetylene from methane and comprising a unit for dissolving acetylene in solvent or a unit for extracting the acetylene by the pressure swing absorption (PSA) and PSA unit for separating hydrogen from the remnants of the methane.

The input and output modules are parts manufactured from metal, heat-resistant plastic, or ceramic. Their job is to create localized gas flows in the area adjacent to the electrodes as the gas enters into the discharge chamber and then leaves it through the holes in these modules. During this process, localized velocity fields are created in the area adjacent to the electrodes (this is different than the gas/gas mixture velocity V), and, if necessary, gas can be blown onto the electrodes, and the gas can be made to move in a spiral so as to form reverse vortex in the discharge chamber.

The rotation of gas in the discharge chamber is created to stabilize the area where the plasma channels are created in the center of the discharge chamber and to prevent the plasma channels from "sticking" to the wall of the reactor. This sticking of plasma channels to the reactor wall is an unwanted and dangerous phenomenon that can lead to the destruction of the walls of the reaction chamber due to overheating. The sticking effect happens as a result of uneven heating of the walls of the discharge chamber and can thus be prevented by directing a gas swirl through the chamber with the help of tangent holes in the input and output modules. This serves to even out the temperatures in the reactor and causes the formation of plasma channels that follow trajectories near to the closest distance between the cathode and the anode.

High-voltage power supply unit 5 maintains enough of a voltage on the electrodes to cause a breakdown and the formation of a plasma channel between electrodes 6 and 7. After the channel heats up, and its resistance drops off, the discharge capacity loses its charge, and the voltage in the discharge gap drops as well, at a certain point passes through zero, and becomes negative due to the inductance in the circuit. At this point, the energy being generated in the plasma channel is close to zero. It takes some time for the discharge capacity to acquire the voltage sufficient for the next breakdown. This time is determined by the parameters of power supply unit 5, which ensures the necessary pause between the pulsed electrical discharges. The next plasma channel forms in a different place and does not affect the reaction products ensuring they reach ideal tempering conditions. The described picture is similar to a pulse-periodic spark discharge, but in this case the lifetime of the plasma channel and their repetition frequency are two times lower, which provides the qualities necessary for application in the described device for plasma-chemical conversion.

Figure 3:
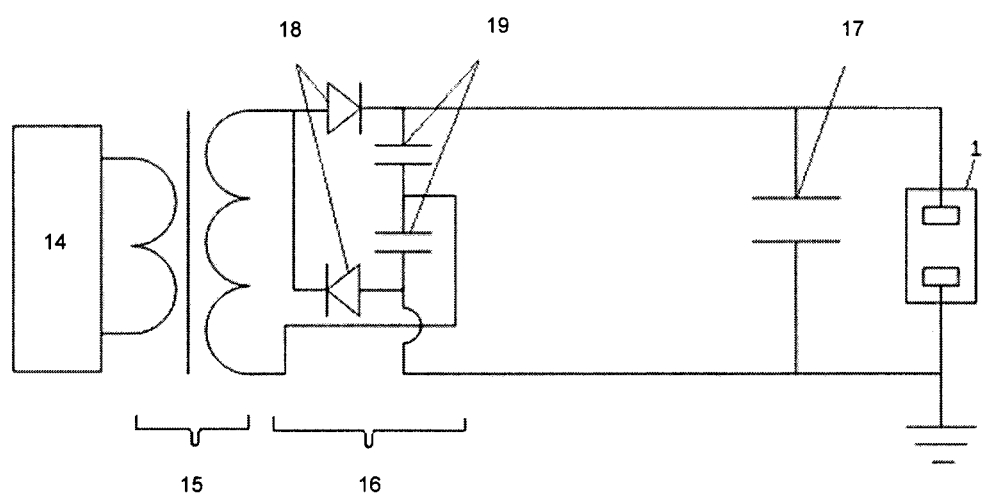
FIG. 3 depicts the electrical circuit diagram of the high-voltage power supply unit for creating pulsed electrical discharges.

For a sample electrical circuit diagram of high-voltage power supply unit 5 used in the device to generate pulsed electrical discharges, see FIG. 3.

The high-voltage power supply unit comprises frequency converter 14, high-voltage high-frequency transformer 15, voltage doubling circuit 16, and output pulse capacitor 17. Voltage doubling circuit 16 comprises high voltage diodes 18 and high voltage capacitors 19.

High-voltage transformer 15 and voltage doubling circuit 16 based on diodes 18 and capacitors 19 operate as limiters on the charging current of output pulse capacitor 17. The charging current can be controlled by changing the frequency of the high voltage fed into the unit or the frequency of the impulses generated by power frequency converter 14. Once the output pulse capacitor has been charged to a voltage sufficient for an interelectrode gap breakdown of plasma-chemical reactor 1, output pulse capacitor 17 discharges through the plasma channel that forms in the process. The capacitance of capacitor 17 should ideally be greater than $I*100$ mkF, where I is the average discharge current.

Once the plasma channel has been extinguished, the process repeats itself. The high repetition frequency ensures the necessary degree of conversion of the reagents and the productivity of the reactor.

In the experiment, 100 pF capacitors were used as capacitors 19 in voltage doubling circuit 16. Frequency converter 14 generated a frequency of 60 kHz or 120 kHz. Output pulse capacitor 16 had a capacity of 300 pF. Therefore, stable regimes of ignition and extinction of plasma channels were obtained, with a frequency of 30 kHz or 60 kHz, respectively. The effective inductance of the circuit of output pulse capacitor 16 through the plasma channel in plasma-chemical reactor 1 was 0.5 µH, 0.125 µH, or 0.03 µH. Meanwhile, the duration of the plasma channel was 180 ns, 80 ns, and 30 ns, respectively.

Examples of the results obtained during the experiment are described below.

EXAMPLE 1

Production of acetylene from a 50/50 mixture of methane and hydrogen at atmospheric pressure. The density was 0.4 kg/m$^3$. The average discharge current was set to 0.4 A. The average gas flow velocity in the discharge chamber was 11.5 m/s. Therefore, the ratio of the flow velocity to the average discharge current was:

$\rho*V^2/I^2=330.6\ J/(m^3*A^2)$, and fell within the target range.

During the experiment, a pure form of electrical discharge as described above was obtained, and the energy cost of acetylene molecule production was 8 eV per molecule.

EXAMPLE 2

Production of acetylene from a 50/50 mixture of methane and hydrogen. The density was 0.38 kg/m3. The average discharge current was set to 0.4 A. The average gas flow velocity in the discharge chamber was 3.5 m/s. Therefore, the ratio of the flow velocity to the average discharge current was:

$\rho*V^2/I^2=29\ J/(m^3*A^2)$, which falls outside the target range.

During the experiment, the discharge took the form of a continuous never-ceasing plasma filament connecting the electrodes—a contracted glow discharge in a flow of gas. The energy cost of producing a molecule of acetylene was 32 eV per molecule.

EXAMPLE 3

Production of acetylene from a 50/50 mixture of methane and hydrogen at an absolute pressure of 1.5 atm. The density was 0.57 kg/m3. The average discharge current was set to 0.4 A. The average gas flow velocity in the discharge chamber was 12 m/s. Therefore, the ratio of the flow velocity to the average discharge current was:

$\rho*V^2/I^2=513\ J/(m^3*A^2)$, which falls outside the target range.

During the experiment, the optimal form of electrical discharge as described above was obtained, and the energy cost of acetylene molecule production was 10.5 eV per molecule.

The invention claimed is:

1. A method of plasma-chemical conversion of a gas comprising:

generating a flow of said gas through a reaction chamber of a reactor comprising a discharge chamber, electrodes, and input and output modules;

generating a pulsed electrical discharge in the reaction chamber that produces hot plasma channels that connects the electrodes;

wherein a ratio between an average flow velocity of the gas in the reaction chamber to the average discharge current falls within the following range:

$250\ J/(m^3*A^2)\rho<*V^2/I^2<4{,}000\ J/(m^3*A^2)$, where $\rho$ is the density of the gas in the reaction chamber (kg/m3), V is the average flow velocity of the gas in the reaction chamber (m/s), and I is the average current of the pulsed electrical discharge (A); wherein a frequency of said pulsed electrical discharge is between 20 and 300 kHz.

2. The method of claim 1, wherein the lifetime of the hot plasma channel is (10-500) ns, and wherein a temperature of the hot plasma channel is at least 2000° C.

3. The method of claim 1, wherein the flow is a swirled flow.

4. The method of claim 3, wherein said swirled flow comprises reverse vortexes.

5. A device for plasma-chemical conversion of gas comprising a reactor comprising a reaction chamber configured to contain said gas, electrodes located within the chamber, an input module configured to create a flow of said gas within the reaction chamber; an output module, a gas flow regulator, and a high-voltage power supply unit configured to supply a current to said electrodes, so as to generate a pulsed electrical discharge in the reaction chamber in the form of a hot plasma channels that connect the electrodes, wherein said device is configured to control a ratio between an average flow velocity of said gas to said current within a following range:

$250\ J/(m^3*A^2)\rho<*V^2/I^2<4{,}000\ J/(m^3*A^2)$, where $\rho$ is the density of the gas in the reaction chamber (kg/m3), V is the average flow velocity of the gas in the reaction chamber (m/s), and I is the current; wherein a frequency of said pulsed electrical discharge is between 20 and 300 kHz.

6. The device of claim 5, wherein the electrodes are one or more anode-cathode pairs; wherein the high-voltage power supply unit is connected to the one or more anode-cathode pairs through an input of the anode and of the cathode, wherein each electrode has one or more inputs.

7. The device of claim 6, wherein the electrodes are designed as (a) cylinders with a flat bottom, (b) cylinders that have one end with a sharp edge, (c) cylinders with rods or needles sticking out of one end, or (d) a cone with a sharp end and radial holes.

8. The device of claim 5, wherein the input module is configured to create a flow of said gas in a form of a swirling flow.

9. The device of claim 5, further comprising a recuperative heat exchanger and a gas separation unit for recycling and reusing reagents of the gas, wherein said recuperative heat exchanger is in operable communication with the output module.

10. The device of claim 5, further comprising a recycling blower in operable communication with the recuperative heat exchanger and with the reaction chamber, and wherein the recycling blower is configured to introduce an additional flow of said gas within the reaction chamber.

* * * * *